United States Patent [19]

Yamaguchi

[11] Patent Number: 5,324,835

[45] Date of Patent: Jun. 28, 1994

[54] PYRIDAZINOQUINOXALINONES FOR USE AS CHEMILUMINESCENT AGENTS

[75] Inventor: Masatoshi Yamaguchi, Fukuoka, Japan

[73] Assignee: Biosensor Laboratories Co., Ltd., Tokyo, Japan

[21] Appl. No.: 925,691

[22] Filed: Aug. 7, 1992

Related U.S. Application Data

[63] Continuation-in-part of Ser. No. 677,207, Mar. 29, 1991, abandoned.

[30] Foreign Application Priority Data

Mar. 30, 1990 [JP] Japan .................. 2-83318

[51] Int. Cl.$^5$ .......................... C07D 487/04
[52] U.S. Cl. ........................ 544/234; 544/237; 435/7.1; 435/14; 436/98
[58] Field of Search .......................... 544/234

[56] References Cited

U.S. PATENT DOCUMENTS 4,598,044 7/1986 Kricka et al. .................. 544/234

OTHER PUBLICATIONS

Nakahara et al., *Anal. Biochem*, 190 pp. 309-313 (Nov. 1990).
Nakahara et al., *Chemical Abstracts*, vol. 114, No. 20354 (1990).
Arakawa et al., *Chem. Pharm. Bull.* 38 p. 3491 (Nov. 1990).

*Primary Examiner*—Emily Bernhardt
*Attorney, Agent, or Firm*—Browdy and Neimark

[57] ABSTRACT

Compounds useful as luminescent labelling reagents or reagents for determining hydrogen peroxide of the following formula:

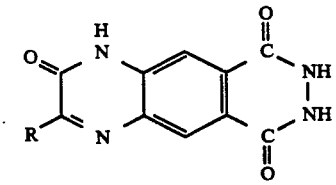

Wherein R is selected from the group consisting of hydrogen, amino, carboxyl, thiol, n-propyl, isopropyl, n-butyl, sec-butyl, benzyl, carboxyethyl, tert-butyl, and
—$(CH_2)_{n1}CH_3$ wherein n is 0 or an integer of 1-15;
—$(CH_2)_{n2}COOH$ wherein $n_2$ is 0 or an integer of 1-5;
—$CH_2SH$; —$CH_2X_1$ wherein X is Br, Cl or F;
—$(CH_2)_{n3}NH_2$ wherein $n_3$ is an integer of 1-5;

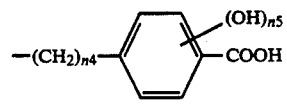

wherein $n_4$ is 0 or 1 and $n_5$ is 0 or

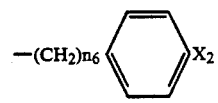

wherein $n_6$ is 0 or 1 and $X_2$ is H, Br, Cl, F or I; and
—$(CH_2)_{n7}R_1$ wherein $n_7$ is 0 or an integer of 1-5 and $R_1$ is selected from COCl, $CON_3$, $CONHNH_2$ or 1 Claim, 3 Drawing Sheets

PYRIDAZINOQUINOXALINONES FOR USE AS CHEMILUMINESCENT AGENTS

The present application is a continuation-in-part of application Ser. No. 07/677,207, filed Mar. 29, 1991, and now abandoned, the entire contents of which are hereby incorporated by reference.

FIELD OF THE INVENTION

This invention relates to novel compounds represented by the following general formula(I):

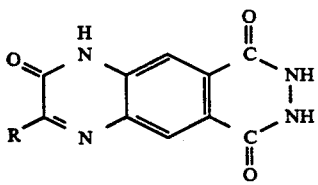

Wherein R is selected from the group consisting of hydrogen, amino, carboxyl, thiol, n-propyl, isopropyl, n-butyl, sec-butyl, benzyl, carboxyethyl, tert-butyl, and
—$(CH_2)_{n1}CH_3$ wherein n is 0 or an integer of 1-15;
—$(CH_2)_{n2}COOH$ wherein $n_2$ is 0 or an integer of 1-5;
—$CH_2SH$; —$CH_2X_1$ wherein X is Br, Cl or F;
—$(CH_2)_{n3}NH_2$ wherein $n_3$ is an integer of 1-5;

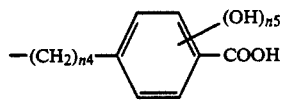

wherein
$n_4$ is 0 or 1 and $n_5$ is 0 or 1;

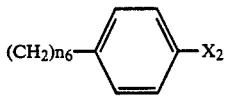

wherein
$n_6$ is 0 or 1 and $X_2$ is H, Br, Cl, F or I; and
—$(CH_2)_{n7}R_1$
wherein
$n_7$ is 0 or an integer of 1-5 and $R_1$ is selected from COCl, $CON_3$, $CONHNH_2$ or

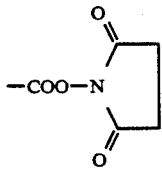

More particularly, it relates to quinoxalinone compounds represented by the general formula (I) which are useful as, for example, luminescent labelling reagents or reagents for determining hydrogen peroxide.

BACKGROUND OF THE INVENTION

There have been reported several derivatization regents for use in determination of α-keto acids by spectroscopic or fluorescent methods in connection with liquid chromatography.

C. Hemming and C. J. Gubler proposed to determine an α-keto acid by a spectroscopic method using 2,4-dinitrophenylhydrazine (*Anal. Biochem.* 92:31, 1979). Regarding the determination of keto acids by a fluorescent method, on the other hand, some workers have reported using 4'-hydrazino-2-stilbazole (cf. T. Hirata, M. Kai, K. Kohashi and Y. Ohkura, *J. Chromatogr.* 226:25, 1981) and o-phenylenediamine (cf. J. C. Liao, N. E. Hoffman, J. J. Barboriak and D. A. Roth, *Clin. Chem.* 2:802, 1977; and T. Hayashi, H,. Tsuchiya and H. Naruse, *J. Chromatogr.* 273:245, 1983). Although each of these reported methods fives a substantially high sensitivity, it is impossible thereby to determine an α-keto acid at a femtomol (fmcl: $10^{-15}$ mol) level.

The present inventors formerly synthesized 1,2-diamino-4,5-dimethoxybenzene and 1,2-diamino-4,5-methylenedioxybenzene each as a fluorescent analysis reagent for α-keto acids having a high sensitivity and a high selectivity. For the former reagent, refer to S. Hara, Y. Takemori, T. Iwata, M. Yamaguchi, M. Nakamura and Y. Ohkura, Anal. Chem. Acta. 172:167, 1985; and S. Hara, M. Yaaguchi, M. Nakamura and Y. Ohkura, *Chem. Pharm. Bull.* 33:3493, 1985. For the latter reagent, reference is made to M. Nakamura, S. Hara, M. Yamaguchi, Y. Takemori and Y. Ohkura, *Chem. Pharm. Bull.* 35:687, 1985. The present inventors have attempted to apply these reagents to liquid chromatography and have thus succeeded in determining α-keto acids at a femtomol level. These reagents have been used for determining α-keto acids contained in human urine and serum, as disclosed in S. Hara, Y. Takemori, M. Yamaguchi, N. Nakamura and Y. Ohkura, *J. Chromatog.* 344:33, 1985.

Recently, techniques for chemiluminescent detection have been introduced into liquid chromatographic analyses. As a result, there have been reported several reagents which react with amino acids, amine or carboxylic acids and thus convert these compounds into chemiluminescent derivatives. For reagents for amino acids, refer to S. R. Spurlin and M. M. Cooper, *Anal. Lett.* 19:2277, 1986; reagents for amines, T. Kawasaki, M. Maeda and A. Tsuji, *J. Chromatogr.* 328:121, 1985. For reagents for carboxylic acids, refer to T. Kawasaki, M. Maeda, and A. Tsuji, *J. Chromatogr.* 328:121, 1985; H. Yuki, H. Azuma, M. Maeda and H Kawasaki, *Chem. Pharm. Bull.* 36:1905, 1988; and H. Karatani, J. Takano, S. Morishita, M. Yoshida and M. Sato, *Bunseki Kagaku* 38:59, 1989.

As described above, attempts have been recently made to determine α-keto acids by spectroscopic or fluorescent methods. However, there has been reported hitherto no reagent required for sensitively and selectively determining a trace amount of an α-keto acid by using chemiluminescence.

The present inventor has conducted extensive studies on a reagent whereby a trace amount of an α-keto acid can be selectively determined by taking advantage of chemiluminescence. As a result, he has discovered that intense chemiluminescence is generated by reacting a quinoxalinone compound, which is obtained by the reaction of an keto acid with 4,5-diaminophthalhydrazide dihydrochloride (hereinafter referred to simply as 4,5-DPJ:2HCl), with hydrogen peroxide in an alkaline polar medium in the presence of potassium hexacyanoferrate (III). Thus, he has separately applied for a patent based upon this finding, on the same date as the parent of the present application, as a novel process for determining an keto acid.

The above chemical reaction may be represented by the following formula:

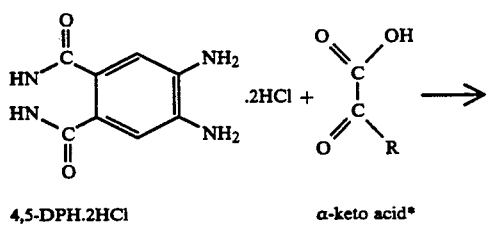

4,5-DPH.2HCl          α-keto acid*

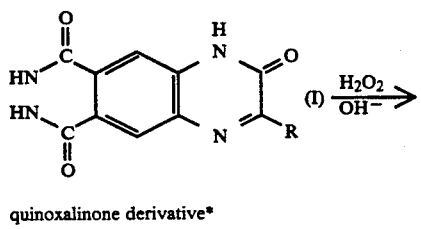

quinoxalinone derivative*

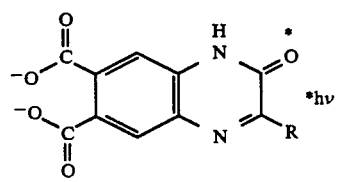

Note: *:R represents a group selected from the group consisting of hydrogen, amino, carboxyl, thiol, n-propyl, isopropyl, n-butyl, sec-butyl, benzyl, carboxyethyl, tert-butyl, and —$(CH_2)_{n1}CH_3$ wherein
n is 0 or an integer of 1-15;

—$(CH_2)_{n2}COOH$ wherein
$n_2$ is 0 or an integer of 1-5;

—$CH_2SH$; —$CH_2X_1$ wherein X is Br, Cl or F;

—$(CH_2)_{n3}NH_2$ wherein
$n_3$ is an integer of 1-5;

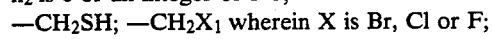

wherein
$n_4$ is 0 or 1 and $n_5$ is 0 or 1;

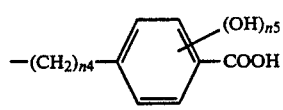

wherein
$n_6$ is 0 or 1 and $X_2$ is H, Br, Cl, F or I; and

—$(CH_2)_{n7}R_1$ wherein
$n_7$ is 0 or an integer of 1-5 and $R_1$ is selected from $COCl$, $CON_3$, $CONHNH_2$ or

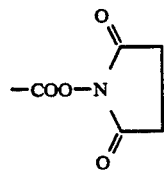

SUMMARY OF THE INVENTION

The present inventor has found that the quinoxalinone compounds of the general formula (I) obtained by the aforesaid chemical reaction are novel compounds which have never been described in any literature that hydrogen peroxide can be determined by using one of these compounds per se as a reaction reagent; and that various substances can be sensitively detected by labelling said substances with one of the aforesaid compounds as a luminescent labelling reagent. Thus, the present invention has been completed based upon these findings.

The present invention relates to quinoxalinone compounds represented by the following formula:

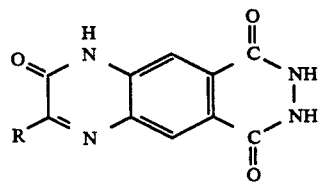

Wherein R is selected from the group consisting of hydrogen, amino, carboxyl, thiol, n-propyl, isopropyl, n-butyl, sec-butyl, benzyl, carboxyethyl, tert-butyl, and —$(CH_2)_{n1}CH_3$ wherein
n is 0 or an integer of 1-15;

—$(CH_2)_{n2}COOH$ wherein
$n_2$ is 0 or an integer of 1-5;

—$CH_2SH$; —$CH_2X_1$ wherein X is Br, Cl or F;

—$(CH_2)_{n3}NH_2$ wherein
$n_3$ is an integer of 1-5;

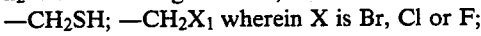

wherein $n_4$ is 0 or 1 and $n_5$ is 0 or 1;

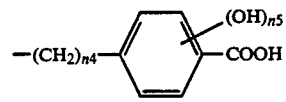

wherein $n_6$ is 0 or 1 and $X_2$ is H, Br, Cl, F or I; and

—$(CH_2)_{n7}R_1$ wherein
$n_7$ is 0 or an integer of 1-5 and $R_1$ is selected from $COCl$, $CON_3$, $CONHNH_2$ or

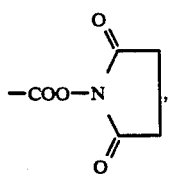

DETAILED DESCRIPTION OF THE PREFERRED EMBODIMENTS

Figure 1:
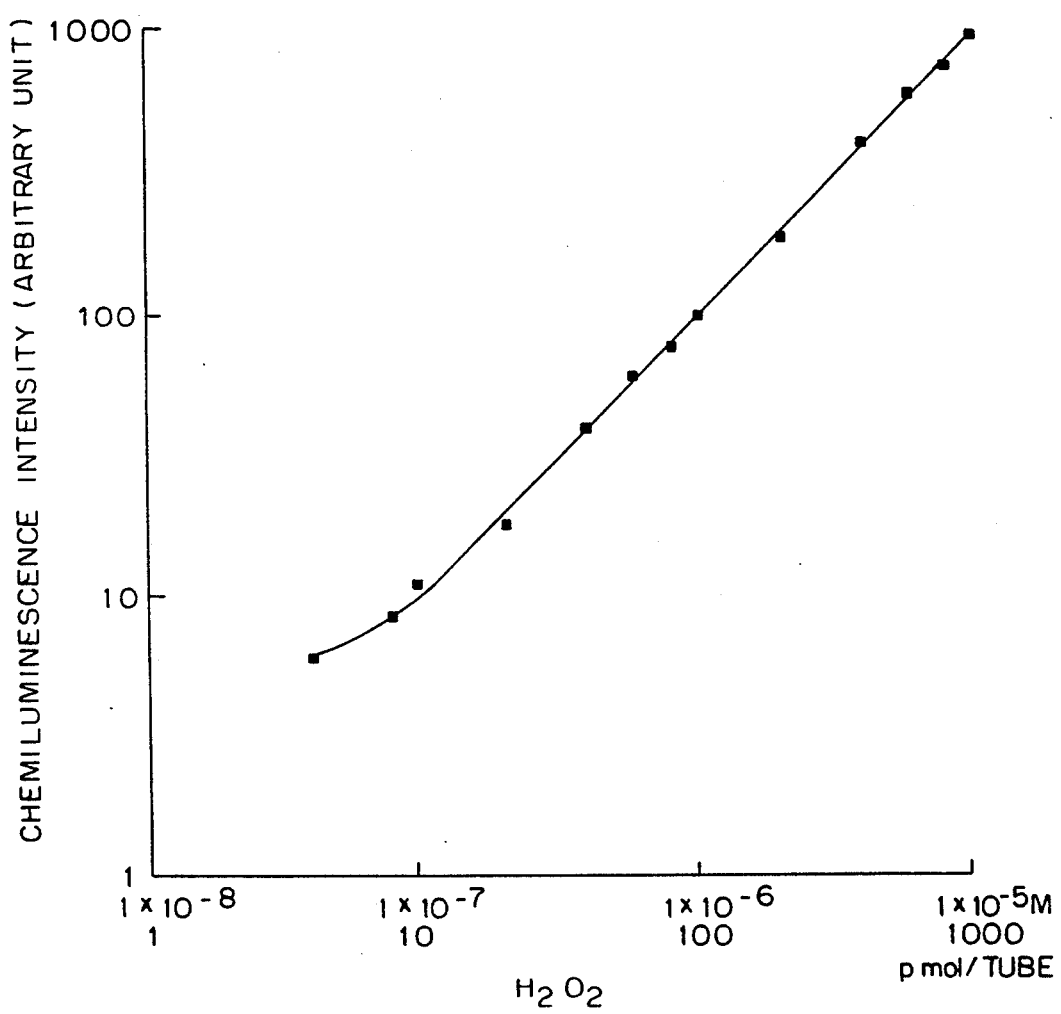
FIG. 1 shows a curve obtained for determination of hydrogen peroxide using a compound according to the present invention.

A described above, R may be any group which does not interfere with chemiluminescence. Examples of R include hydrogen, optionally substituted hydrocarbon, optionally substituted heterocyclic, amino, carboxyl, and thiol. In particular, those groups which can react with alkyl groups phenyl-substituted alkyl groups, amino groups, carboxyl groups thiol groups or alcoholic hydroxyl groups (such as carboxyl groups, carbonyl halides, acid azides, succinimide esters, isothiocyanates, amino group, maleimide groups and acid hydrazides) are useful groups. Examples of functional groups capable of reacting with alcoholic hydroxyl groups are as follows:

—(CH$_2$)$_2$—X wherein n is 0 or an integer; and

X represents a group selected from COOH, COCl, CON$_2$,

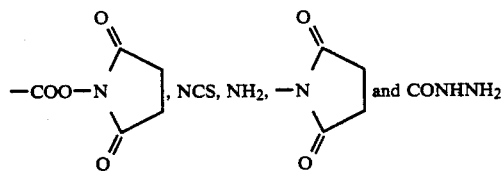

In accordance with the present invention, R may be any group which is defined above. Concrete examples of R are as 1. hydrogen, amino, thiol, —CH$_2$SH, isopropyl, sec-butyl, tert-butyl;
2. —CH$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —(CH$_2$)$_6$CH$_3$, —(CH$_2$)$_7$CH$_3$, —(CH$_2$)$_8$CH$_3$, —(CH$_2$)$_9$CH$_3$, —(CH$_2$)$_{10}$CH$_3$, —(CH$_2$)$_{11}$CH$_3$, —(CH$_2$)$_{12}$CH$_3$, —(CH$_2$)$_{13}$CH$_3$, —(CH$_2$)$_{14}$CH$_3$, —(CH$_2$)$_{15}$CH$_3$.
3. —COOH, —CH$_2$COOH, —(CH$_2$)$_2$COOH, —(CH$_2$)$_3$COOH, —(CH$_2$)$_4$COOH, —(CH$_2$)$_5$COOH.
4. —CH$_2$Br, —CH$_2$Cl, —CH$_2$F.
5. —CH$_2$NH$_2$, —(CH$_2$)$_2$NH$_2$—, —(CH$_2$)$_3$NH$_2$, —(CH$_2$)$_4$NH$_2$, —(CH$_2$)$_5$NH$_2$.

6. 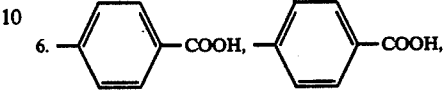

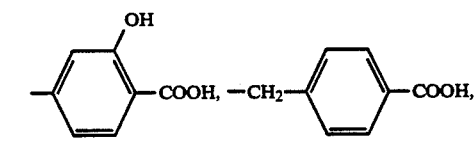

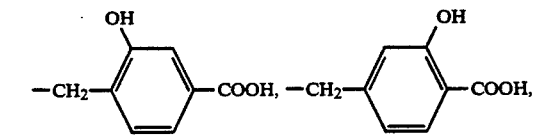

7. 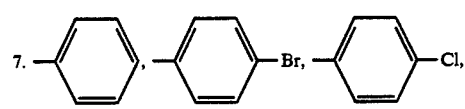

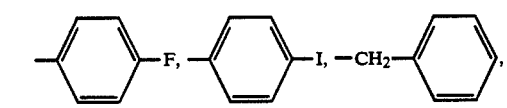

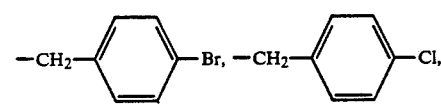

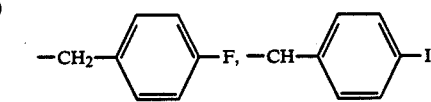

8. —COCl, —CH$_2$—COCl, —(CH$_2$)$_2$—COCl, —(CH$_2$)$_3$—COCl, —(CH$_2$)$_4$—COCl, —(CH$_2$)$_5$—COCl, —CON$_3$, —CH$_2$—CON$_3$, —(CH$_2$)$_2$—CON$_3$, —(CH$_2$)$_3$—CON$_3$, —(CH$_2$)$_4$—CON$_3$, —(CH$_2$)$_5$—CON$_3$, —CONHNH$_2$, —CH$_2$—CONHNH$_2$, —(CH$_2$)$_2$—CONHNH$_2$, —(CH$_2$)$_3$—CONHNH$_2$, —(CH$_2$)$_4$—CONHNH$_2$, —(CH$_2$)$_5$—CONHNH$_2$,

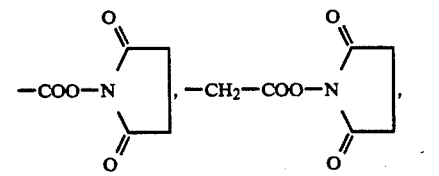

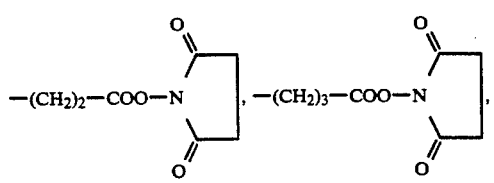

-continued

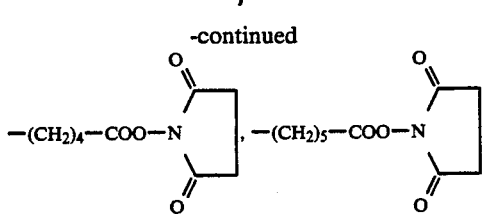

The quinoxalinone compounds of the present invention may be obtained by reacting an keto acid represented by the following formula (II), wherein R is hydrogen, amino, thiol, $CH_2SH$, isopropyl, sec-butyl, tert-butyl;

2. $-CH_3$, $-CH_2CH_3$, $-(CH_2)_2CH_3$, $-(CH_2)_3CH_3$, $-(CH_2)_4CH_3$, $-(CH_2)_5CH_3$, $-(CH_2)_6CH_3$, $-(CH_2)_7CH_3$, $-(CH_2)_8CH_3$, $-(CH_2)_9CH_3$, $-(CH_2)_{10}CH_3$, $-(CH_2)_{11}CH_3$, $-(CH_2)_{12}CH_3$, $-(CH_2)_{13}CH_3$, $-(CH_2)_{14}CH_3$, $-(CH_2)_{15}CH_3$.

3. $-COOH$, $-CH_2COOH$, $-(CH_2)_2COOH$, $-(CH_2)_3COOH$, $-(CH_2)_4COOH$, $-(CH_2)_5COOH$.

4. $-CH_2Br$, $-CH_2Cl$, $-CH_2F$.

5. $-CH_2NH_2$, $-(CH_2)_2NH_2-$, $-(CH_2)_3NH_2$, $-(CH_2)_4NH_2$, $-(CH_2)_5NH_2$.

6.

[structures of hydroxybenzoic acid derivatives]

7.

[structures of phenyl, bromophenyl, chlorophenyl, fluorophenyl, iodophenyl, benzyl and substituted benzyl groups]

8. $-COCl$, $-CH_2-COCl$, $-(CH_2)_2-COCl$, $-(CH_2)_3-COCl$, $-(CH_2)_4-COCl$, $-(CH_2)_5-COCl$, $-CON_3$, $-CH_2-CON_3$, $-(CH_2)_2-CON_3$, $-(CH_2)_3-CON_3$, $-(CH_2)_4-CON_3$, $-(CH_2)_5-CON_3$, $-CONHNH_2$, $-CH_2-CONHNH_2$, $-(CH_2)_2-CONHNH_2$, $-(CH_2)_3-CONHNH_2$, $-(CH_2)_4-CONHNH_2$, $-(CH_2)_5-CONHNH_2$,

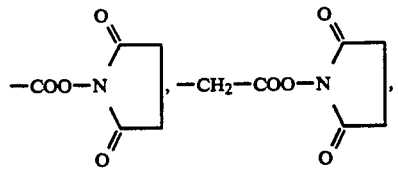

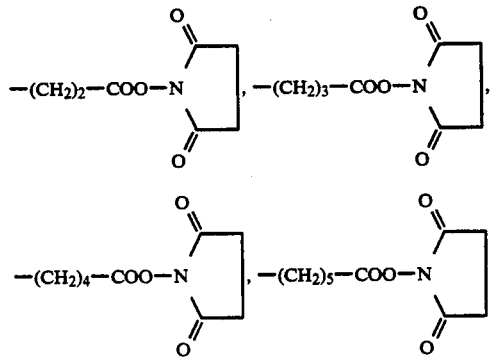

the α-keto acid reactions with 4,5-diaminophthalhydrazide of formula (III) as follows:

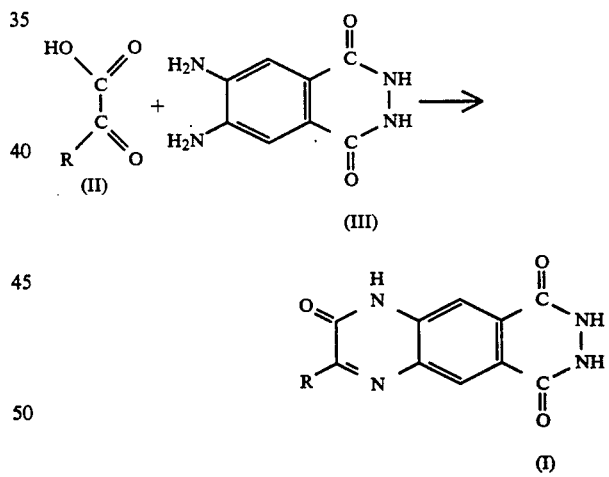

To further illustrate the present invention, and not by way of limitation, the following examples are given:

4,5-diaminophthalhydrazide (0.3 mmol) and each α-keto acid (0.6 mmol) as specified in Table 1 were dissolved in a mixture of hydrochloric acid (2 mol) containing 1.2 mol of -mercapto-ethanol (1.2 mol) and ethanol 1:1, v/v). The obtained mixture was heated in a water bath for 2 hours. After the completion of the heating, the mixture was cooled in ice/water. The precipitate thus formed was collected by filtering and washed with ethanol. Thus the corresponding quinoxalinone derivative was obtained. The yield ranged from 40 to 50% in the case of each α-keto acid.

Tables 1 and 2 show the physicochemical data of the quinoxalinone derivatives thus obtained.

TABLE 1

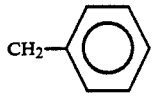

| Ex. No. | Employed α-keto acid | R | m.p. (decomp.) | Chemical formula | Elemental analysis (%) calcd. (found) C | H | N | Appearance |
|---|---|---|---|---|---|---|---|---|
| 1 | α-ketovaleric acid | $CH_2CH_2CH_3$ | 350 | $C_{13}H_{12}N_4O_3$ | 57.35 (57.08 | 4.44 4.46 | 20.58 20.37) | pale green powder |
| 2 | α-ketoisovaleric acid | $CH_3$<br>\|<br>$CHCH_3$ | 355 | $C_{13}H_{12}N_4O_3$ | 57.35 (57.29 | 4.44 4.36 | 20.58 20.70) | pale green powder |
| 3 | α-ketocaproic acid | $CH_2CH_2CH_2CH_3$ | 355 | $C_{14}H_{14}N_4O_3$ | 58.74 (58.64 | 4.93 4.98 | 19.57 19.82) | pale green powder |
| 4 | α-ketoisocaproic acid | $CH_2CHCH_3$<br>\|<br>$CH_3$ | 340 | $C_{14}H_{14}N_4O_3$ | 58.74 (58.74 | 4.93 4.88 | 19.57 19.76) | pale green powder |
| 5 | α-keto-β-methyl- acid | $CHCH_2CH_3$<br>\|<br>$CH_3$ | 345 | $C_{14}H_{14}N_4O_3$ | 58.74 (57.92 | 4.93 5.07 | 19.57 19.27) | pale green powder |
| 6 | α-phenylpyruvic acid | $CH_2$—⟨phenyl⟩ | 352 | $C_{17}H_{12}N_4O_3$ | 63.77 (63.75 | 3.97 3.78 | 17.63 17.49) | pale green powder |
| 7 | α-ketoglutaric acid | $CH_2CH_2COOH$ | 352 | $C_{13}H_{10}N_4O_5$ | 51.66 (51.75 | 3.33 3.27 | 18.54 18.72) | pale green powder |
| 8 | α-ketomalonic acid | COOH | 348 | $C_{11}H_6N_4O_5$ | 48.19 (48.08 | 2.21 2.28 | 20.43 20.57) | pale green powder |

TABLE 2

| Ex. No. | IR (cm$^{-1}$) | MS (m/z) | NMR (in DMSO-D$_6$) (ppm) |
|---|---|---|---|
| 1 | 3420, 3200 1670, 1640 | 273 | 0.99(3H, t, J=7), 1.77(2H, se, J=7), 2.82(2H, t, J=7), 7.85(1H, s), 8.27(1H, s), 11.49(1H×2, br), 12.63(1H, br) |
| 2 | 3430, 3170 1670, 1640 | 273 | 1.27(3H×2, d, J=7), 3.24–3.65(1H, m), 7.88(1H, s), 8.30(1H, s), 11.40(1H×2, br), 12.71(1H, br) |
| 3 | 3420, 3200 1675, 1640 | 287 | 0.94(3H, t, J=7), 1.23–1.88(2H×2, m), 2.85(2H, t, J=7), 7.86(1H, s), 8.27(1H, s), 11.08(1H×2, br), 12.65(1H, br) |
| 4 | 3420, 3170 1670, 1620 | 287 | 0.97(3H×2, d, J=7), 2.20–2.55(1H, m), 2.74(2H, d, J=7), 7.86(1H, s), 8.28(1H, s), 11.54(1H×2, br), 12.71(1H, br) |
| 5 | 3420, 3175 1670, 1610 | 287 | 0.90(3H, t, J=7), 1.23(3H, d, J=7), 1.40–2.06(3H, m), 7.88(1H, s), 8.30(1H, s), 11.56(1H×2, br), 12.69(1H, br) |
| 6 | 3420, 3200 1675, 1620 | 321 | 4.19(2H, s), 7.11–7.69(5H, m), 7.86(1H, s), 8.27(1H, s), 11.46(1H×2, br), 12.78(1H, s) |
| 7 | 3420, 3200 1670, 1640 | 303 | — |
| 8 | 3420, 3200 1670, 1620 | 275 | — |

The quinoxalinone compounds of the present invention react with hydrogen peroxide in an alkaline solvent in the presence of potassium hexacyanoferrate (III), thus showing chemiluminescence. By utilizing this characteristic, the compounds of the present invention can be applied to the following purposes.

1. Reagent for determining hydrogen peroxide

1) The compounds of the present invention are available as a reagent for determining hydrogen peroxide formed by an enzymatic reaction (applicable to the measurement of the activity of an enzyme and to the assay of a substrate of an enzyme).

2) The compounds can be used as a reagent for determining hydrogen peroxide formed by a chemical reaction-

2. Luminescent labeling reagent

1) The compounds of the present invention can be used as a reagent for labeling, for example, proteins, amino acids, saccharides, lipids, vitamins, hormones and drugs. These substances to be determined, which have been labeled with a compound of the present invention, may be detected and determined by separating by high-performance liquid chromatography (HPLC) and then reacting with hydrogen peroxide.

2) The compounds may be used for labeling, for example, antigens, antibodies, ligands, receptors, DNAs and RNAs. By using these substances labeled with a compound of the present invention, materials capable of undergoing a biochemical reaction with these substances can be assayed.

The following Experimental Examples illustrate determinations that can readily be conducted using the compounds of the present invention.

EXPERIMENTAL EXAMPLES

Experimental Example 1: Determination of hydrogen peroxide

A 100 μl solution ($1 \times 10^{-5}$M) of a quinoxalinone derivative given in Table 1 was added to a 100 μl sample or an $H_2O_2$ standard solution to give a mixture. A 100 μl solution of microperoxidase (obtained from Sigma), which solution was prepared using 0.1M phosphate buffer so that the concentration thereof might be $1 \times 10^{-5}$M, was injected into the mixture. The total mount of luminescence which was generated for 30 seconds between 30 and 60 seconds immediately after the injection of the microperoxidase solution, was monitored by a TD-4000 lumiphotometer.

In the case where any quinoxalinone derivative was used, a straight line which passes through the origin of the coordinates was obtained as a calibration curve in the monitored range of $7-66 \times 10^{-8}$M (7-66 p mol/tube) to $1 \times 10^{-5}$M (1 n mol/tube) (FIG. 1). The detection limit is 7-66 p mol/tube (Table 3).

Experimental Example 2: Determination of the level of glucose in serum

To serum diluted one in 100 with distilled water or 50 μl of a glucose standard solution were added 50 μl of glucose oxidase (Sigma, 80 units/ml) and 2.0 ml of a 0.1M phosphate buffer pH 7.0). The mixture was incubated at 37° C. for 30 minutes. A 100 μl aliquot of the resultant reaction mixture was used as a sample. The aliquot was subjected to the operations in accordance with the same method for determination of hydrogen peroxide as described in Experimental Example 1.

Figure 2:
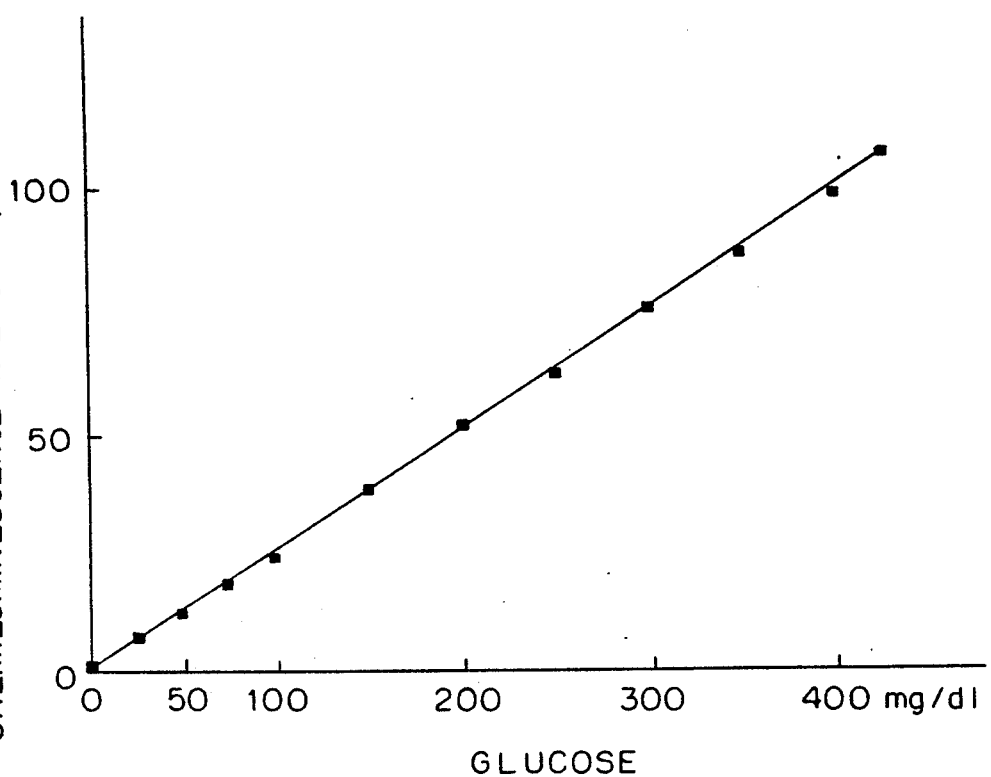
FIG. 2 shows a curve for detection of glucose in serum using a compound according to the present invention.

The results show that a calibration curve obtained is a straight line which passes through the origin of the coordinates and the detection sensitivity was 25 mg/dl (FIG. 2).

Experimental Example 3: Determination of a quinoxalinone derivative

To a 100 μl aqueous solution of a quinoxalinone derivative was added 0.05 M hydrogen peroxide prepared with 2N NaOH. 0.03M potassium ferricyanide ($K_3Fe(CN)_6$) which was prepared with 2 N NaOH was injected into the mixture. The total amount of luminescence which was generated for 10 seconds immediately after the injection of the potassium ferricyanide, was monitored by a TD-4000 lumiphotometer.

Figure 3:
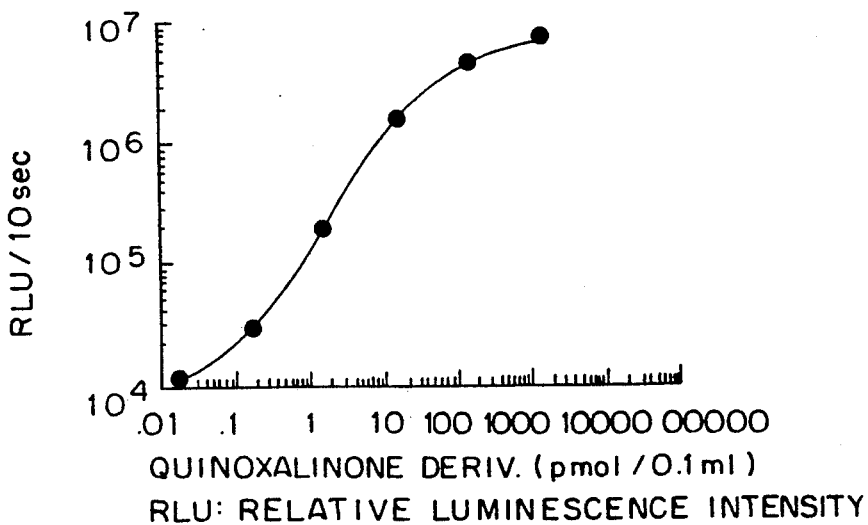
FIG. 3 shows a curve obtained for detection of a quinoxalinone derivative according to the present invention.

It has been found that a quinoxalinone derivative can be determined in the range of 0.1 p mol/0.1 ml to 1 n mol/0.1 ml (FIG. 3).

Experimental Example 4: Purification of anti rG-CSF antibodies

A saturated ammonium sulfate solution (10 ml) was gradually added to rabbit anti rG-CSF serum (10 ml) under the conditions of stirring and cooling with ice. The mixture was stirred for a further two hours followed by centrifugation at 17,000 rpm for 20 minutes. The precipitate was dissolved with 5 ml of 0.1M borate buffer (pH 8.0) containing 0.9% NaCl. The dissolved precipitate was poured into an Ultrogel AcA44 column (5×90 cm) equilibrated previously with the buffer and eluted with the same buffer. The eluate was dispensed to give fractions each having 5 ml thereof. The absorbance at 280 nm of each fraction was determined. The fractions containing substances having molecular weight of about 150,000 were collected and rabbit anti rG-CS IgG was obtained.

Anti rG-CSF monoclonal antibodies were purified by the same operations as those in the purification method of rabbit anti rG-CS IgG.

Experimental Example 5: preparation of antigen- or antibody-binding plates

The purified rabbit anti rG-CS IgG was diluted with a 50 mM sodium hydroencarbonate solution (pH 9.6) to give a dilute solution having the concentration of 0 02 m/ml. The dilute solution was poured on microtiter plates each in an amount of 0.05 ml. The plates were incubated overnight at 4° C. and thereafter unadsorbed antibody was removed from the plate by sucking the antibody solution and washing the plates with 0.2 ml of a 0.9% NaCl solution (three times). To the plates was added 0.2 ml of a phosphate buffer (pH 8.0) containing 1% SSA, 0.9% NaCl and 0.1% $NaN_3$. The plates thus obtained were kept at 4° C. for use as antibody-binding plates.

rG-CSP was diluted with a 50 mM sodium hydrogencarbonate solution (pH 9.6) to give a dilute solution having the concentration of 0.01 mg/ml. The dilute solution was poured on microtiter plates each in an amount of 0.05 ml. The plates were subjected to the same subsequent operations as those used in the preparation of the antibody-binding plates mentioned above. Thus antigen-binding plates were prepared.

Experimental Example 6: Preparation of quinoxalinone derivative labeled antibodies The quinoxalinone derivative (compound VII in Table 1; 100 mg) was suspended in N,N-dimethylformamide. The suspension was stirred at 60° C. for 3 hours and thereafter incubated at room temperature followed by centrifugation at 3000 rpm for 5 minutes. To 2 ml of the supernatant thus obtained were added 8.5 mg of N-hydroxysuccinimide and 0.1 ml of N,N-diisopropylcarbodiimide under stirring, and reaction among these substances was carried out at room temperature for one hour. The reaction solution (0.3 ml was dropped little by little into 3.2 ml of a monoclonal antibody solution (3 mg/ml, 0.1 M phosphate buffer, pH 7.5) under stirring, and reaction between them was carried out at room temperature for 4 hours. The reaction mixture was passed through a 0.22 μm filter in order to remove the insoluble matters. Thereafter the filtered mixture was poured into a pD-10 column equilibrated beforehand with 0.1M phosphate buffer (pH 7.5). The mixture was eluted with the same buffer and the protein fractions were collected to obtain quinoxalinone derivative labeled antibodies.

Experimental Example 7: Determination of rG-CSF by competitive assay

On an antigen-binding plate was dropped 0.05 ml of an antibody standard solution (anti rG-CSF monoclonal antibody) diluted with 50 mM Tris-hydrochloric acid buffer [pH 8.0, hereinafter referred to as "the reaction buffer") containing 150 mM sodium chloride, 0.25SSA, 0.05% Tween 20 and 0.1% sodium azide or 0.05 ml of a sample. After the mixture was reacted at 4° C. for 16 hours, the reaction solution was removed and the plate was washed with 0.2 ml of 20 mM Tris-hydrochloric acid buffer (pH 8.0, hereinafter referred to as "the wash") containing 0.005% benzalkonium chloride (three times). To the plate were added 0.05 ml of quinoxalinone derivative labeled antibodies diluted with the reaction buffer and the mixture was reacted at room temperature for 90 minutes. After the reaction was completed, the plate was washed with the wash (four times). To the plate was added 0.1 ml of a 2% sodium dodecyl sulfate (SDS) solution and the plate was incubated for 10 minutes. After the antibodies were dissociated from the antigen-binding plate, the total weight thereof was poured into a measuring vial.

Chemiluminescence reaction was initiated by concurrently injecting 0.1 ml of 1N NaOH solution containing 25 mM hydrogen peroxide and 0.1 ml of 1N NaOH solution containing 15 mM potassium ferricyanide into the vial. The total amount of chemiluminescence generated between from 5 to 25 seconds after addition of the reagents, was monitored.

Figure 4:
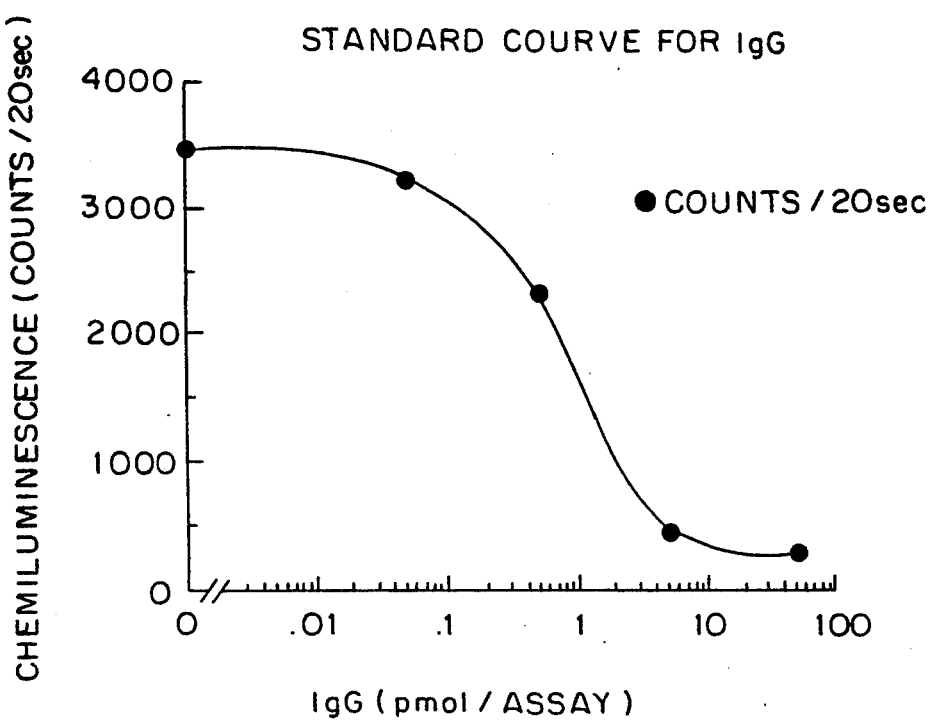
FIG. 4 shows a curve for determination of anti rG-CSF antibodies using a compound of the present invention.

The results show that anti rG-CSF antibodies can he determined in the range of 0.1-10 p mol/assay (0.05 ml) and the detection sensitivity is 0.1 p mol/assay (0.05 ml (FIG. 4).

Experimental Example 8: Determination of G-CSP by sandwich assay

To an antibody-binding plate was added 0.05 ml of an rG-CSF standard solution diluted with the reaction buffer as used in Experimental Example 7 or 0.05 ml of a sample. After the mixture was reacted at room temperature for 2 hours, the plate was washed with the wash in Experimental Example 7 (three times). To the washed plate were added 0.05 ml of quinoxalinone derivative labeled antibodies diluted with the reaction buffer. After the mixture was reacted at room temperature for 90 minutes, the plate was washed with the wash (four times). To the plate was added 0.1 ml of a 2% SDS solution and the plate was incubated for 10 minutes. After the antigens and antibodies were dissociated from the antibody-binding plate, the total weight thereof was poured into a measuring vial.

Chemiluminescence reaction was initiated by concurrently injecting 0.1 ml of 1N NaOH solution containing 25 mM hydrogen Peroxide and 0.1 ml of 1N NaOH solution containing 15 mM potassium ferricyanide into the vial. The total amount of chemiluminescence generated between from 5 to 25 seconds after addition of the reagents, was monitored.

Figure 5:
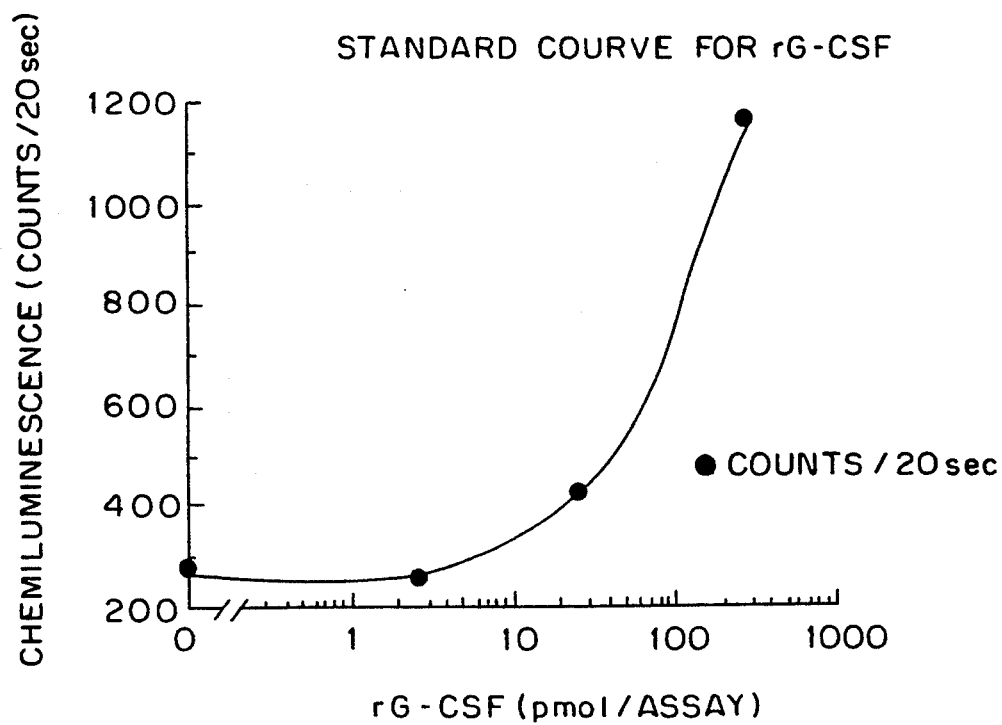
FIG. 5 shows a curve for monitoring G-CSF using a compound according to the present invention.

The results show that G-CSF can be monitored in the range of between from 5-300 p mol/assay (0.05 ml) and the detection sensitivity is 5 p mol assay (0.05 ml (FIG. 5).

TABLE 3

Relative CL Intensities (RCl) and Detection Limits (DL) of Compounds I-VII

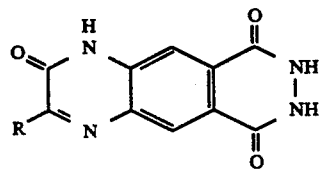

| Compound No. | R | RCl[a,b] | Blank[a] | DL[c] (pmol/tube) |
|---|---|---|---|---|
| I | $CH_2CH_2CH_3$ | 100 | 7 | 20 |
| II | $CHCH_3$<br>\|<br>$CH_3$ | 63 | 4 | 19 |
| III | $CH_2CH_2CH_2CH_3$ | 82 | 2 | 7 |
| IV | $CH_2CHCH_3$<br>\|<br>$CH_3$ | 71 | 16 | 66 |
| V | $CHCH_2CH_3$<br>\|<br>$CH_3$ | 137 | 4 | 8 |
| VI | $CH_2$—Ph | 105 | 16 | 46 |
| VII | $CH_2CH_2COOH$ | 79 | 2 | 8 |

[a] Integrated CL intensity of compound I was taken as 100.
[b] $H_2O_2$ concentration: $1 \times 10^{-6}$ M
[c] DL: S/N = 3

What is claimed is:

1. Quinoxalinone compounds represented by the following formula:

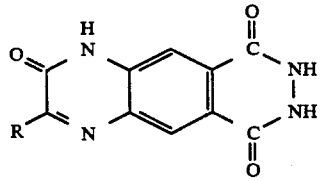

wherein R is selected from the group consisting of hydrogen, amino, carboxyl, thiol, n-propyl, iso-propyl, n-butyl, sec-butyl, benzyl and carboxyethyl.

* * * * *